United States Patent
Nakamura

(10) Patent No.: US 9,937,001 B2
(45) Date of Patent: Apr. 10, 2018

(54) THERAPEUTIC TREATMENT APPARATUS

(71) Applicant: OLYMPUS CORPORATION, Tokyo (JP)

(72) Inventor: Kotaro Nakamura, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 572 days.

(21) Appl. No.: 14/571,867

(22) Filed: Dec. 16, 2014

(65) Prior Publication Data

US 2015/0100056 A1 Apr. 9, 2015

Related U.S. Application Data

(63) Continuation of application No. PCT/JP2013/063823, filed on May 17, 2013.

(30) Foreign Application Priority Data

Jun. 28, 2012 (JP) .................................. 2012-145622

(51) Int. Cl.
*A61B 18/14* (2006.01)
*A61B 18/12* (2006.01)
(Continued)

(52) U.S. Cl.
CPC ........ *A61B 18/1206* (2013.01); *A61B 18/085* (2013.01); *A61B 18/1445* (2013.01);
(Continued)

(58) Field of Classification Search
CPC .............. A61B 18/1206; A61B 18/085; A61B 18/1445; A61B 2018/00702;
(Continued)

(56) References Cited

U.S. PATENT DOCUMENTS 4,685,459 A * 8/1987 Koch ................. A61B 18/1206
219/234
5,443,463 A * 8/1995 Stern ..................... A61B 18/14
606/51
(Continued)

FOREIGN PATENT DOCUMENTS

EP 0 694 291 A1 1/1996
JP 2001190561 A 7/2001
(Continued)

OTHER PUBLICATIONS

English translation of International Preliminary Report on Patentability together with the Written Opinion dated Jan. 8, 2015 received in related International Application No. PCT/JP2013/063823.
(Continued)

*Primary Examiner* — Michael Peffley
(74) *Attorney, Agent, or Firm* — Scully, Scott, Murphy & Presser, P.C.

(57) ABSTRACT

A therapeutic treatment apparatus includes a first heat transfer unit, a second heat transfer unit, a first heat generating element, a second heat generating element, a temperature acquisition unit which acquires a first temperature of the first heat generating element and a second temperature of the second heat generating element, a control unit and an electric power input unit. The control unit determines a first control value and a second control value concerning the electric power input to the first and second heat generating element based on a lower one of the first temperature and the second temperature. The electric power input unit inputs an electric power to the first and second generating element based on the first and second control value.

6 Claims, 13 Drawing Sheets

(51) Int. Cl.
*A61B 18/08* (2006.01)
*A61B 18/00* (2006.01)

(52) U.S. Cl.
CPC ........... *A61B 2018/00702* (2013.01); *A61B 2018/00791* (2013.01); *A61B 2018/00797* (2013.01); *A61B 2018/1455* (2013.01)

(58) Field of Classification Search
CPC .......... A61B 2018/00791; A61B 2018/00797; A61B 2018/1455; A61B 18/082; A61B 18/08; A61B 2017/00084; A61B 18/1492; A61B 2018/00559; A61B 2018/00589–2018/00892
USPC .............................................. 606/27, 28, 31
See application file for complete search history.

(56) References Cited

U.S. PATENT DOCUMENTS

| | | | | |
|---|---|---|---|---|
| 2002/0183734 A1* | 12/2002 | Bommannan | ...... | A61B 18/1445 606/32 |
| 2003/0171747 A1* | 9/2003 | Kanehira | ........... | A61B 17/3201 606/45 |
| 2007/0203481 A1* | 8/2007 | Gregg | ................ | A61B 18/1233 606/34 |
| 2008/0187989 A1 | 8/2008 | McGreevy et al. | | |
| 2009/0248002 A1 | 10/2009 | Takashino et al. | | |

FOREIGN PATENT DOCUMENTS

| | | |
|---|---|---|
| JP | 2001269352 A | 10/2001 |
| JP | 2009-247893 A | 10/2009 |

OTHER PUBLICATIONS

Chinese Office Action dated Mar. 14, 2016 in related Chinese Patent Application No. 201380026138.2.
Extended Supplementary European Search Report dated Feb. 10, 2016 from related European Application No. 13 81 0857.6.
Japanese Office Action dated Feb. 2, 2016 from related Japanese Patent Application No. 2012-145622, together with an English language translation.
International Search Report dated Jun. 25, 2013 received in PCT/JP2013/063823.

* cited by examiner

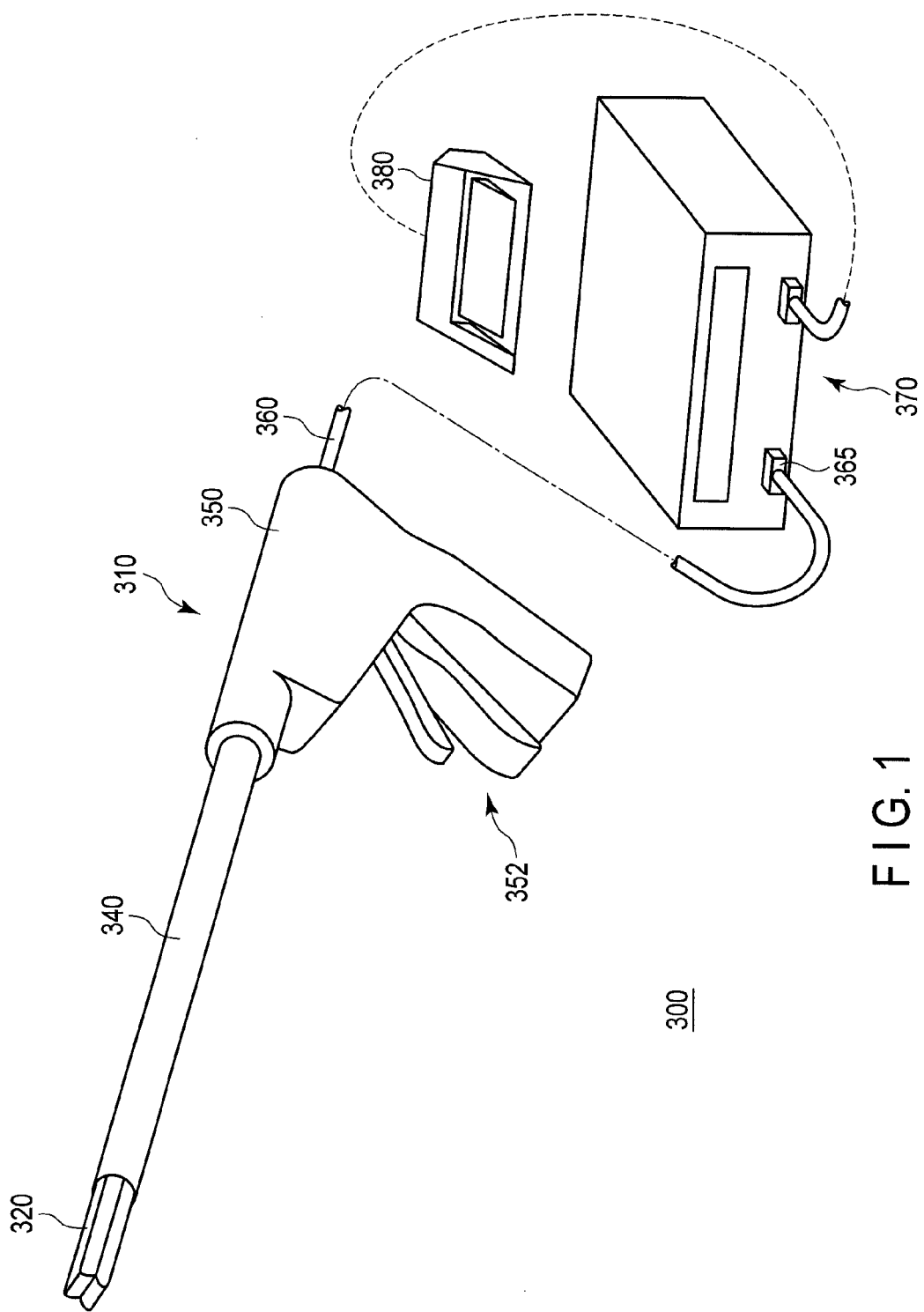
F I G. 1

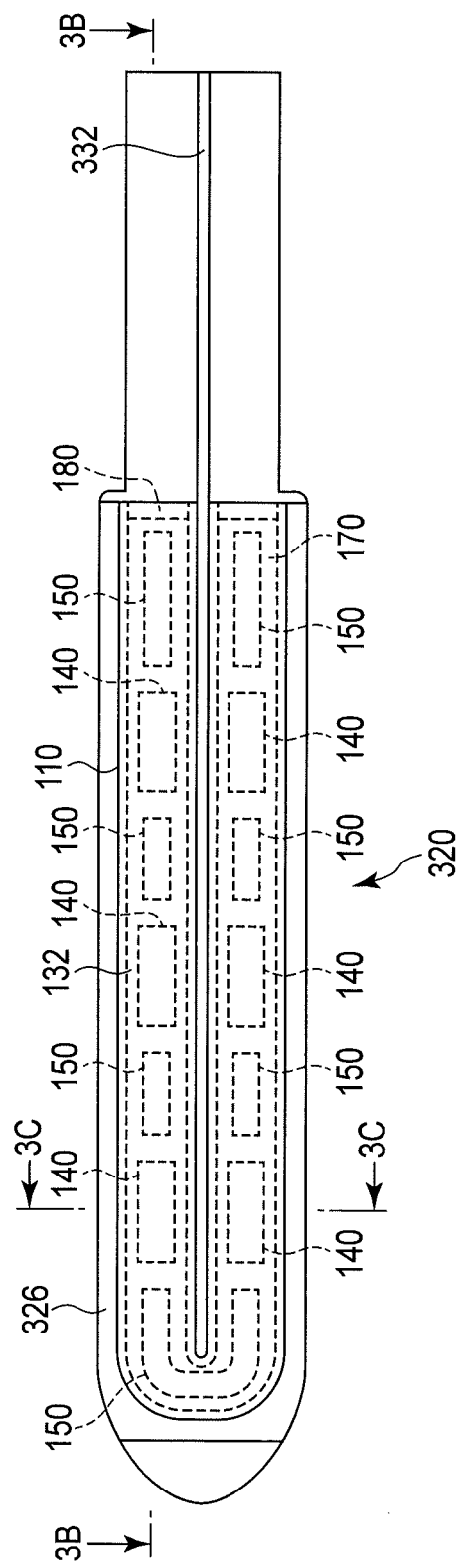
F I G. 3A

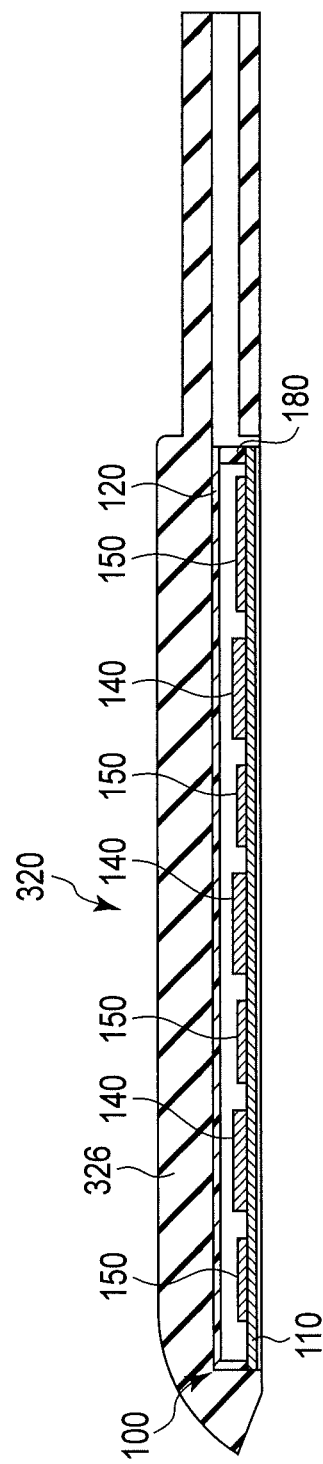
F I G. 3B

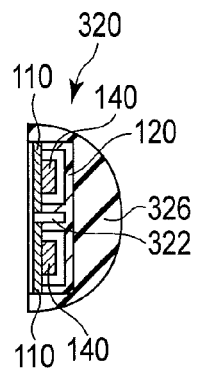
F I G. 3C
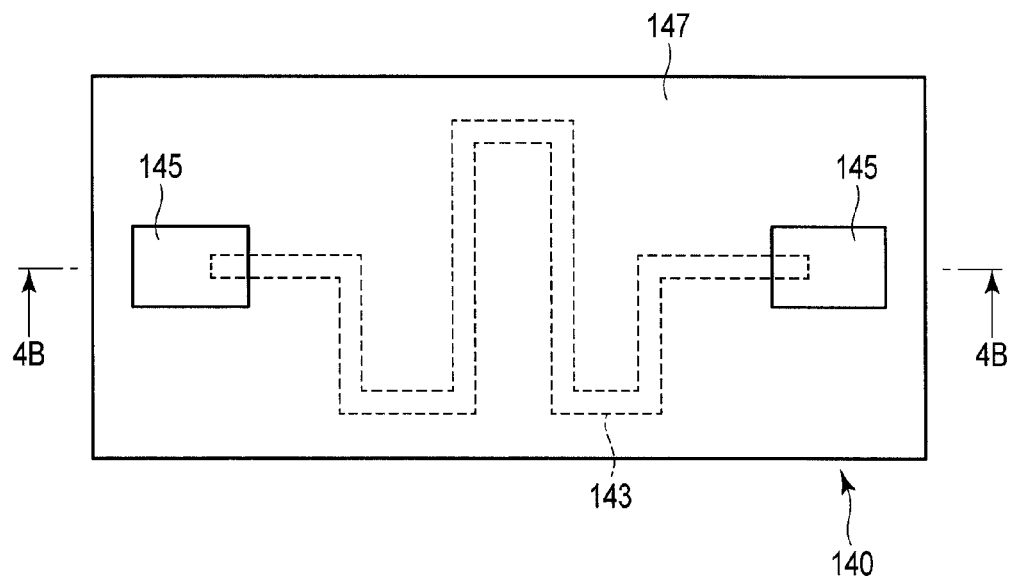
F I G. 4A

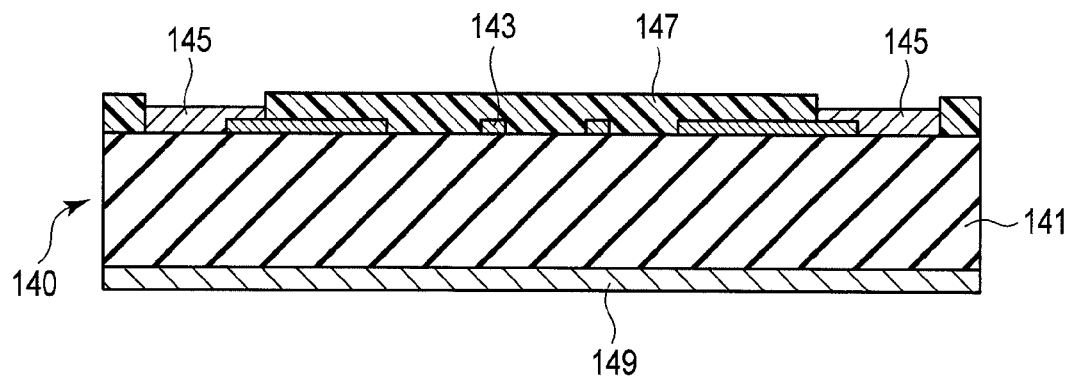
F I G. 4B
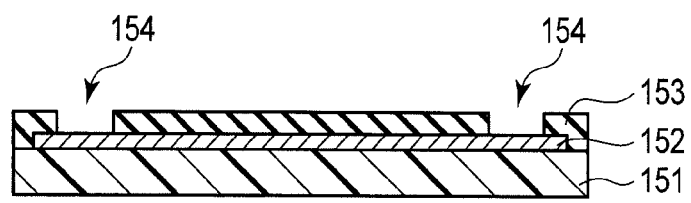
F I G. 5

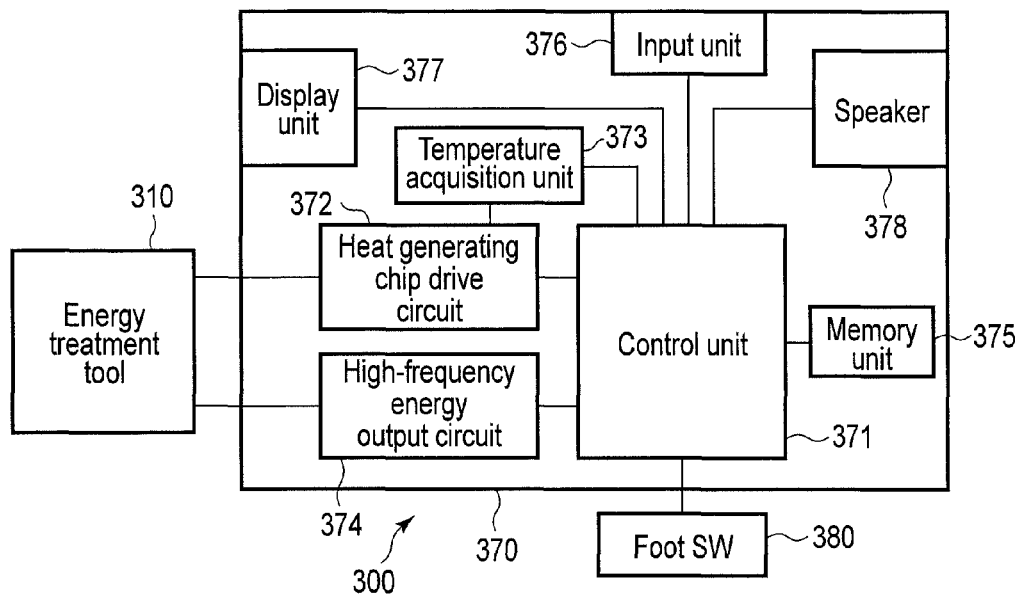
F I G. 7
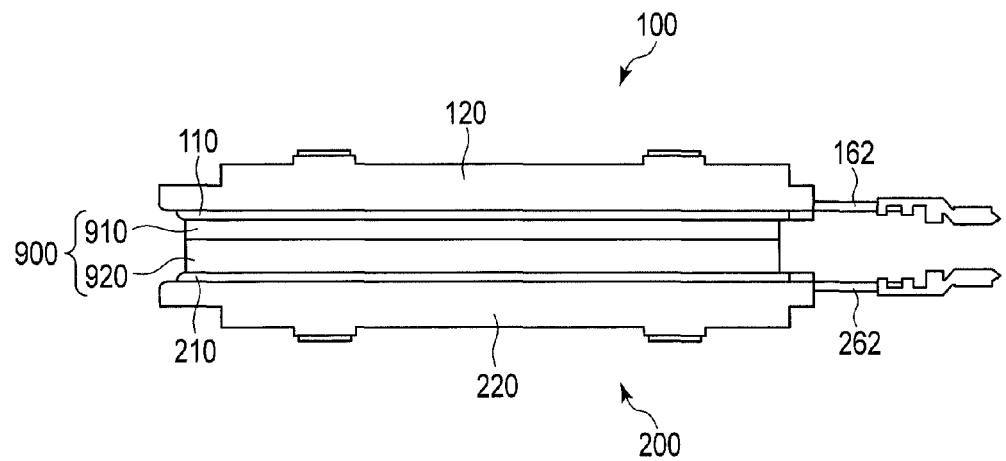
F I G. 8

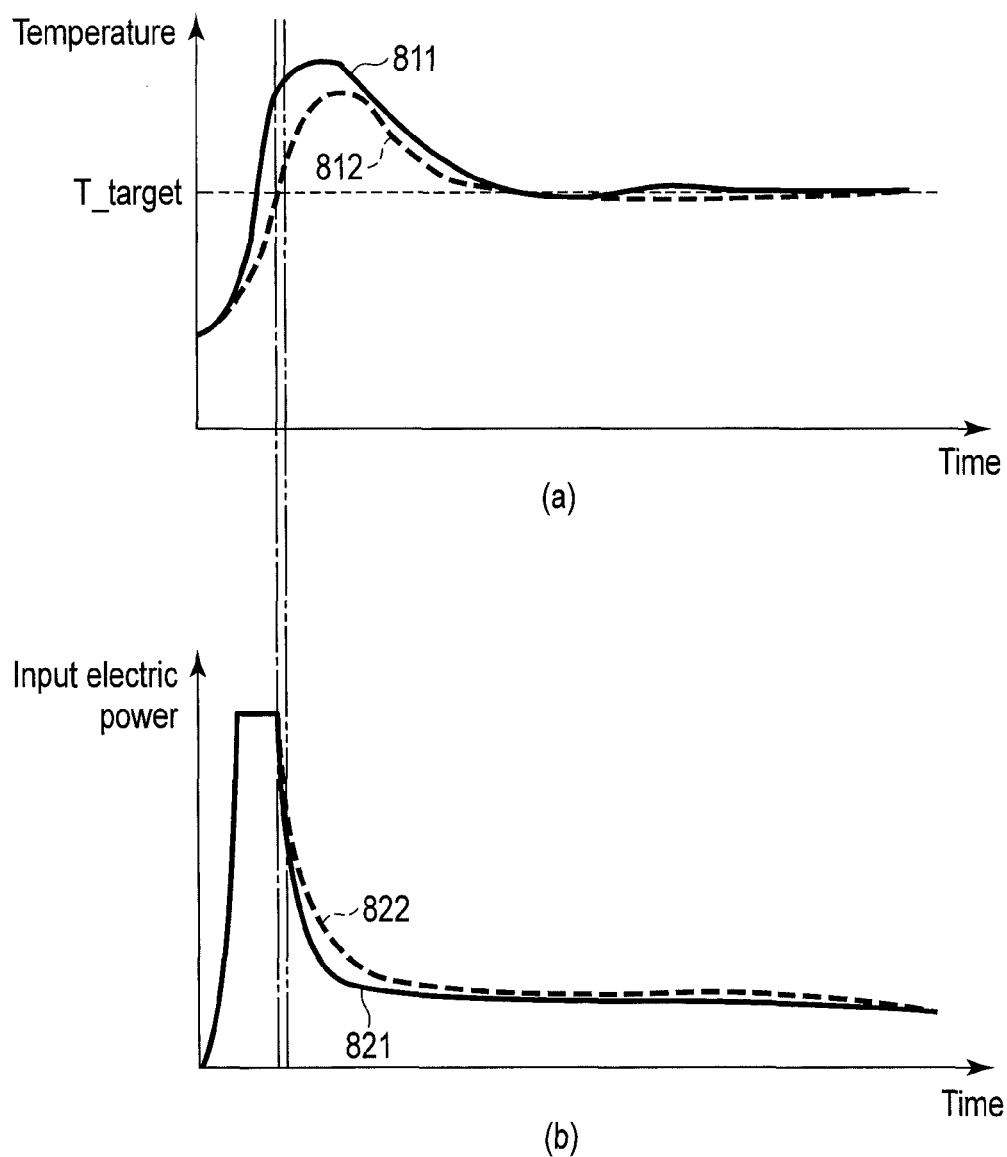
F I G. 12

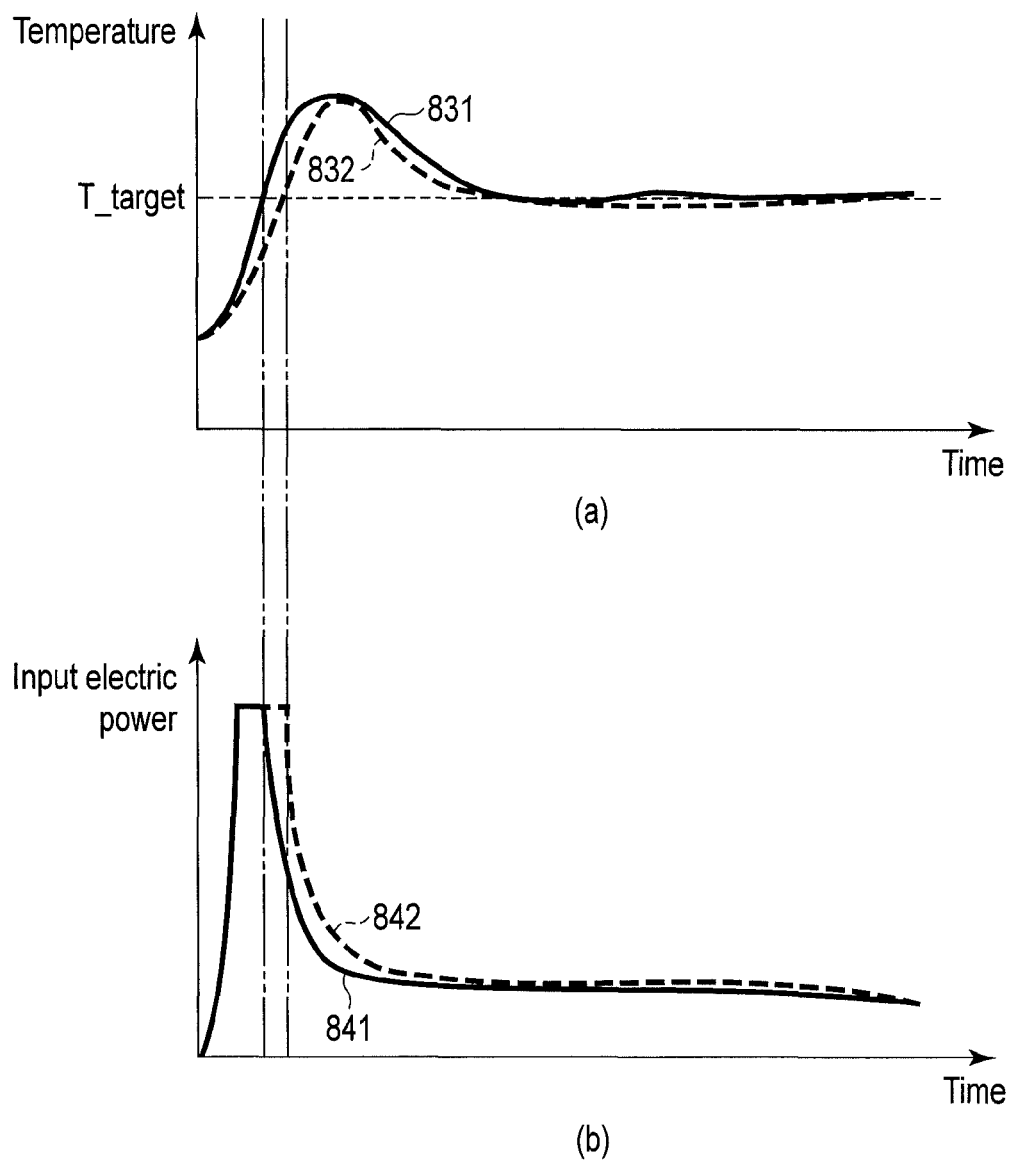
F I G. 13

THERAPEUTIC TREATMENT APPARATUS

CROSS-REFERENCE TO RELATED APPLICATIONS

This application is a Continuation Application of PCT Application No. PCT/JP2013/063823, filed May 17, 2013 and based upon and claiming the benefit of priority from prior Japanese Patent Application No. 2012-145622, filed Jun. 28, 2012, the entire contents of all of which are incorporated herein by reference.

BACKGROUND OF THE INVENTION

1. Field of the Invention

The present invention relates to a therapeutic treatment apparatus.

2. Description of the Related Art

In general, there is known a therapeutic treatment apparatus used to perform a medical treatment on a biological tissue by using high-frequency energy or thermal energy. For example, Jpn. Pat. Appln. KOKAI Publication No. 2001-190561 discloses a technology concerning a therapeutic treatment apparatus configured to heat and coagulate a biological tissue. This therapeutic treatment apparatus includes a pair of openable/closable jaws that grip a biological tissue. These jaws have heat conduction units, each of which is provided with a heat generator that generates heat by energization. When the heat conduction units are heated, the gripped biological tissue is heated. Jpn. Pat. Appln. KOKAI publication No. 2001-190561 discloses a technology that concerns acquiring temperatures of the heat conduction units and a biological tissue based on a change in electric resistance value of each heat generator and controlling the heat conduction units to a predetermined temperature.

BRIEF SUMMARY OF THE INVENTION

According to an aspect of the present invention, a therapeutic treatment apparatus that heats a biological tissue and provides a treatment includes: a first heat transfer unit which comes into contact with the biological tissue and transfers heat to the biological tissue; a second heat transfer unit which relatively moves with respect to the first heat transfer unit, grips the biological tissue with the first heat transfer unit, and transfers the heat to the biological tissue; a first heat generating element which is arranged on the first heat transfer unit and heats the first heat transfer unit when electric power is input; a second heat generating element which is arranged on the second heat transfer unit and heats the second heat transfer unit when electric power is input; a temperature acquisition unit which acquires a first temperature that is a temperature of the first heat transfer unit and a second temperature that is a temperature of the second heat transfer unit; a control unit which compares the first temperature with the second temperature and determines a first control value concerning the electric power input to the first heat generating element and a second control value concerning the electric power input to the second heat generating element based on a lower one of the first temperature and the second temperature; and an electric power input unit which inputs the electric power to the first heat generating element based on the first control value and inputs the electric power to the second heat generating element based on the second control value.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 1 is a schematic view showing a configuration example of a therapeutic treatment system according to an embodiment of the present invention;

FIG. 3A is a schematic view showing a structural example of a first holding member of the holding unit according to the embodiment of the present invention and is also a plan view;

FIG. 3B is a schematic view showing the structural example of the first holding member of the holding unit according to the embodiment of the present invention and is also a longitudinal cross-sectional view taken along a line 3B-3B depicted in FIG. 3A;

FIG. 3C is a schematic view showing the structural example of the first holding member of the holding unit according to the embodiment of the present invention and is also a transverse cross-sectional view taken along a line 3C-3C depicted in FIG. 3A;

FIG. 4A is a top view showing an outline of a structural example of a heat generating chip according to the embodiment of the present invention;

FIG. 4B is a view showing the outline of the structural example of the heat generating chip according to the embodiment of the present invention and is also a cross-sectional view taken along a line 4B-4B depicted in FIG. 4A;

FIG. 5 is a cross-sectional view showing an outline of a structural example of a wiring member according to the embodiment of the present invention;

FIG. 7 is a block diagram showing a structural example of a control device according to the embodiment of the present invention;

FIG. 8 is a schematic view showing an example of a state that a biological tissue is gripped by a first electrode unit and a second electrode unit;

FIG. 12 is a view showing an example of temperature changes of electrode units and a change in power input to the electrode units according to the embodiment of the present invention; and FIG. 13 is a view showing an example of temperature changes of electrode units and a change in power input to the electrode units according to a comparative example.

DETAILED DESCRIPTION OF THE INVENTION

Figure 2A:
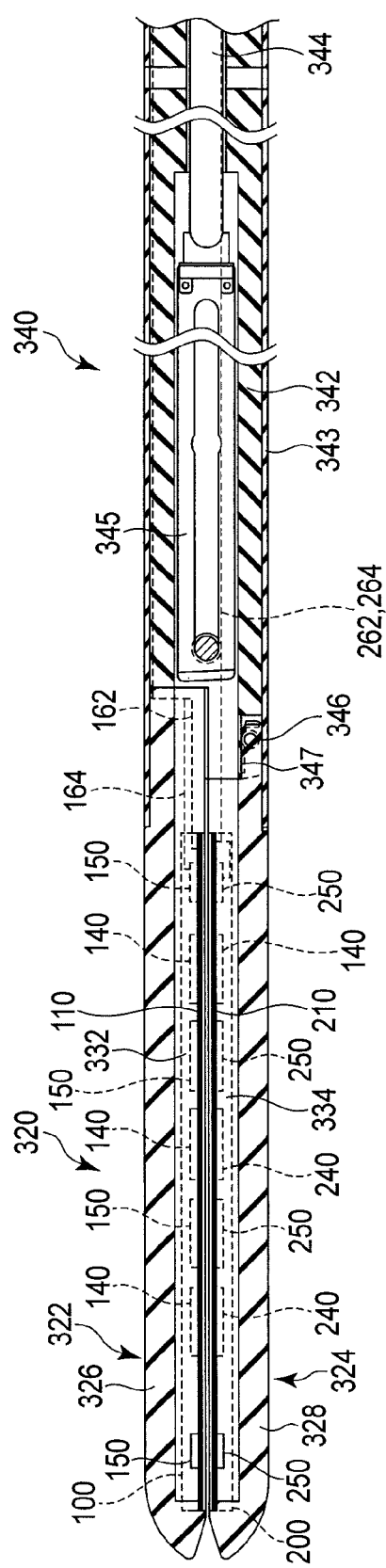
FIG. 2A is a schematic view of a cross section showing a structural example of a shaft and a holding unit of an energy treatment tool according to the embodiment of the present invention and is also a view showing a state that the holding unit is closed.

An embodiment according to the present invention will now be described with reference to the drawings. A therapeutic treatment apparatus according to the present invention is an apparatus used for a treatment of a biological tissue. This therapeutic treatment apparatus allows high-frequency energy and thermal energy to act on a biological tissue. As shown in FIG. 1, a therapeutic treatment apparatus 300 includes an energy treatment tool 310, a control device 370, and a foot switch 380.

The energy treatment tool 310 is a linear type surgical treatment tool that is configured to penetrate through, e.g., an abdominal wall to perform a treatment. The energy treatment tool 310 has a handle 350, a shaft 340 disposed to the handle 350, and a holding unit 320 provided at a tip of the shaft 340. The holding unit 320 is a treatment unit that is openable/closable, grips a biological tissue as a treatment target, and performs a treatment such as coagulation and incision on the biological tissue. In the following description, the holding unit 320 side will be referred to as a distal end side, and the handle 350 side will be referred to as a proximal end side. The handle 350 includes operation knobs 352 used for operating the holding unit 320. Further, the handle 350 includes a non-illustrated non-volatile memory that stores a characteristic value and other information concerning the energy treatment tool 310. It is to be noted that a shape of the energy treatment tool 310 described here is an example as a matter of course, and any other shape may be adopted as long as the same function is provided. For example, a shape like a pair of forceps may be used, or the shaft may be bent.

The handle 350 is connected to the control device 370 through a cable 360. Here, the cable 360 and the control device 370 are detachably connected to each other through a connector 365. That is, the therapeutic treatment apparatus 300 is configured in such a manner that the energy treatment tool 310 can be replaced in accordance with each treatment. The foot switch 380 is connected to the control device 370. The foot switch 380 operated by foot may be substituted by a switch operated by hand or any other switch. When an operator operates a pedal of the foot switch 380, ON/OFF of supply of energy to the energy treatment tool 310 from the control device 370 is switched.

Figure 2B:
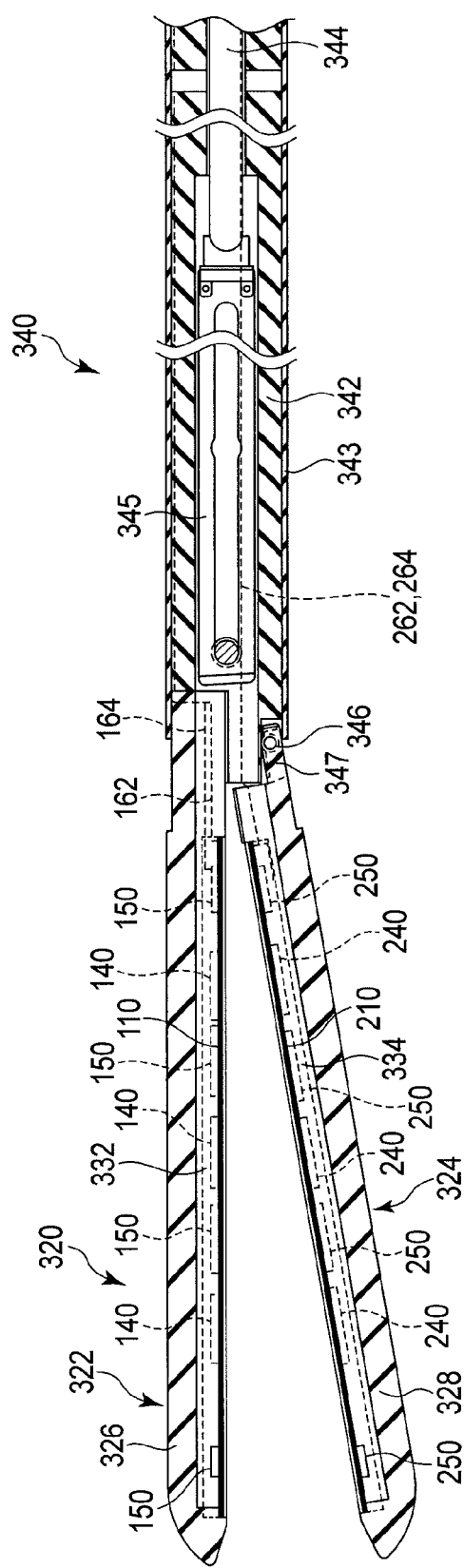
FIG. 2B is a schematic view of a cross section showing the structural example of the shaft and the holding unit of the energy treatment tool according to the embodiment of the present invention and is also a view showing a state that the holding unit is opened.

FIG. 2A and FIG. 2B show an example of a configuration of the holding unit 320 and the shaft 340. FIG. 2A shows a state that the holding unit 320 is closed, and FIG. 2B shows a state that the holding unit 320 is opened. The shaft 340 includes a tube body 342 and a sheath 343. The tube body 342 is fixed to the handle 350 at a proximal end portion thereof. The sheath 343 is arranged on an outer periphery of the tube body 342 to be slidable along an axial direction of the tube body 342.

The holding unit 320 is arranged at a distal end portion of the tube body 342. The holding unit 320 includes a first holding member 322 and a second holding member 324. A base portion of the first holding member 322 is fixed to the distal end portion of the tube body 342 of the shaft 340. On the other hand, a base portion of the second holding member 324 is supported at the distal end portion of the tube body 342 of the shaft 340 by a support pin 346 to allow it to rotate. Therefore, the second holding member 324 rotates around an axis of the support pin 346 and opens or closes with respect to the first holding member 322.

In a state that the holding unit 320 is closed, a cross-sectional shape when the base portion of the first holding member 322 is fitted to the base portion of the second holding member 324 is a circular shape. The second holding member 324 is biased by an elastic member 347 such as a leaf spring so that it can open with respect to the first holding member 322. When the sheath 343 is slid to the distal end side with respect to the tube body 342 and the base portion of the first holding member 322 and the base portion of the second holding member 324 are covered with the sheath 343, the first holding member 322 and the second holding member 324 are closed against a bias force of the elastic member 347, as shown in FIG. 2A. On the other hand, when the sheath 343 is slid toward the proximal end side of the tube body 342, the second holding member 324 opens with respect to the first holding member 322 by the bias force of the elastic member 347 as shown in FIG. 2B.

A first high-frequency electrode conducting line 162 connected to a later-described first high-frequency electrode 110 and a second high-frequency electrode conducting line 262 connected to a second high-frequency electrode 210 are inserted in the tube body 342. Further, a pair of first heat generating chip conducting lines 164 connected to later-described heat generating chips 140 as heat generating members and a pair of second heat generating chip conducting lines 264 connected to heat generating chips 240 are inserted in the tube body 342.

In the tube body 342, a drive rod 344 connected to one of the operation knobs 352 on the proximal end side is installed to be movable along the axial direction of the tube body 342. A sheet-like cutter 345 having a blade formed on the distal end side is installed on the distal end side of the drive rod 344. When one of the operation knobs 352 is operated, the cutter 345 is moved along the axial direction of the tube body 342 through the drive rod 344. When the cutter 345 is moved toward the distal end side, the cutter 345 is accommodated in a first cutter guide groove 332 and a second cutter guide groove 334, which will be described later, formed in the holding unit 320.

The holding unit 320 will now be described with reference to FIG. 3A, FIG. 3B, and FIG. 3C. As shown in FIG. 3B and FIG. 3C, the first cutter guide groove 332 for guiding the cutter 345 is formed in the first holding member 322. The first high-frequency electrode 110 formed of, e.g., a copper sheet is provided in the first holding member 322. The first high-frequency electrode 110 is configured to come into contact with a biological tissue on one main surface (which will be referred to as a first main surface hereinafter) thereof. The first high-frequency electrode 110 has the first cutter guide groove 332, and hence its planar shape is U-shaped, as shown in FIG. 3A. As shown in FIG. 2A and FIG. 2B, the first high-frequency electrode conducting line 162 is electrically connected to a second main surface that is an opposite side of the first main surface of the first high-frequency electrode 110. The first high-frequency electrode 110 is connected to the control device 370 through this first high-frequency electrode conducting line 162 and the cable 360.

The heat generating chips 140 are arranged on the second main surface of the first high-frequency electrode 110 that does not come into contact with a biological tissue, as will be described later in detail. Further, wiring members 150 for wiring to the heat generating chips 140 are arranged on the second main surface. A first cover member 120 is arranged to cover the heat generating chips 140, wiring lines and other parts including the wiring members 150, and the first high-frequency electrode 110. The first cover member 120 is made of, e.g., a resin. A space between the first high-frequency electrode 110 and the first cover member 120 at the proximal end portion is filled with an end portion sealant 180. It is to be noted that the first cover member 120 and the end portion sealant 180 are omitted in FIG. 2A and FIG. 2B to simplify the drawings. In this manner, a first electrode unit 100 surrounded by the first high-frequency electrode 110 and the first cover member 120 is formed. The first electrode unit 100 is buried and fixed in a first holding member main body 326 having electric insulation and thermal insulation.

As shown in FIG. 2A and FIG. 2B, the second holding member 324 has a shape that is symmetrical with respect to the first holding member 322 and the same configuration as the first holding member 322. That is, the second cutter guide groove 334 is formed in the second holding member 324 at a position where it faces the first cutter guide groove 332. Furthermore, the second high-frequency electrode 210 is provided to the second holding member 324 at a position where it faces the first high-frequency electrode 110. This second high-frequency electrode 210 is configured to come into contact with a biological tissue on one main surface thereof. The second high-frequency electrode 210 is connected to the control device 370 through the second high-frequency electrode conducting line 262 and the cable 360.

Moreover, the same heat generating chips 240 as the heat generating chips 140 are bonded to a surface of the second high-frequency electrode 210 that does not come into contact with a biological tissue. The same second cover member as the first cover member 120 is arranged to cover the heat generating chips 240, wiring lines and other parts including wiring members for connection with the heat generating chips 240, and the second high-frequency electrode 210. Proximal end portions of the second high-frequency electrode 210 and the second cover member are buried with the use of the end portion sealant. In this manner, a second electrode unit 200 surrounded by the second high-frequency electrode 210 and the second cover member 220 is formed. The second electrode unit 200 is buried and fixed in a second holding member main body 328.

The first electrode unit 100 will now be described in detail. It is to be noted that the second electrode unit 200 has the same configuration as the first electrode unit 100 and hence a description of the second electrode unit 200 will be omitted. The heat generating chip 140 will now be described with reference to FIG. 4A and FIG. 4B. Here, FIG. 4A is a top view, and FIG. 4B is a cross-sectional view taken along a line 4B-4B depicted in FIG. 4A. The heat generating chip 140 is formed by using a substrate 141 made of a material having high thermal conductivity such as alumina nitride or alumina. A resistance pattern 143 which is, e.g., a Pt thin film for heat generation is formed on a surface that is one of main surfaces of the substrate 141. Additionally, rectangular electrodes 145 are formed on the surface of the substrate 141 near two short sides of a rectangle. Here, the electrodes 145 are connected to respective end portions of the resistance pattern 143. An insulating film 147 made of, e.g., polyimide is formed on the surface of the substrate 141 including the upper side of the resistance pattern 143 except for portions where the electrodes 145 are formed.

A bonding metal layer 149 is formed on an entire back surface of the substrate 141. The electrodes 145 and the bonding metal layer 149 are multilayer films made of, e.g., Ti, Cu, Ni, and Au. The electrodes 145 and the bonding metal layer 149 are strong enough to resist soldering and the like. The bonding metal layer 149 is provided in such a manner that bonding can be stabilized at the time of, e.g., soldering each heat generating chip 140 to the first high-frequency electrode 110.

Each heat generating chip 140 is arranged on a surface (a second main surface) of the first high-frequency electrode 110 on the opposite side of the surface (the first main surface) that comes into contact with a biological tissue. Here, each heat generating chip 140 is fixed by soldering the surface of the bonding metal layer 149 to the second main surface of the high-frequency electrode 110. A conductive paste may be used for this fixation. It is to be noted that each heat generating chip 240 fixed to the second high-frequency electrode 210 has the same configuration as each heat generating chip 140 described above.

Each wiring member 150 is, e.g., a flexible printed circuit board. FIG. 5 is a cross-sectional view showing an outline of the wiring member 150. As shown in this drawing, a wiring line 152 made of, e.g., copper is formed on a substrate 151 made of, e.g., polyimide. The wiring line 152 is covered with an insulating film 153. However, part of the wiring line 152 is not covered with the insulating film 153, and the exposed wiring line 152 functions as an electrode 154. Although a size or a shape of the wiring member 150 varies as required, a basic configuration is as described above. It is to be noted that a foil-like or plate-like wiring member such as a glass epoxy substrate may be used as the wiring member 150 in place of the flexible circuit board.

Figure 6:
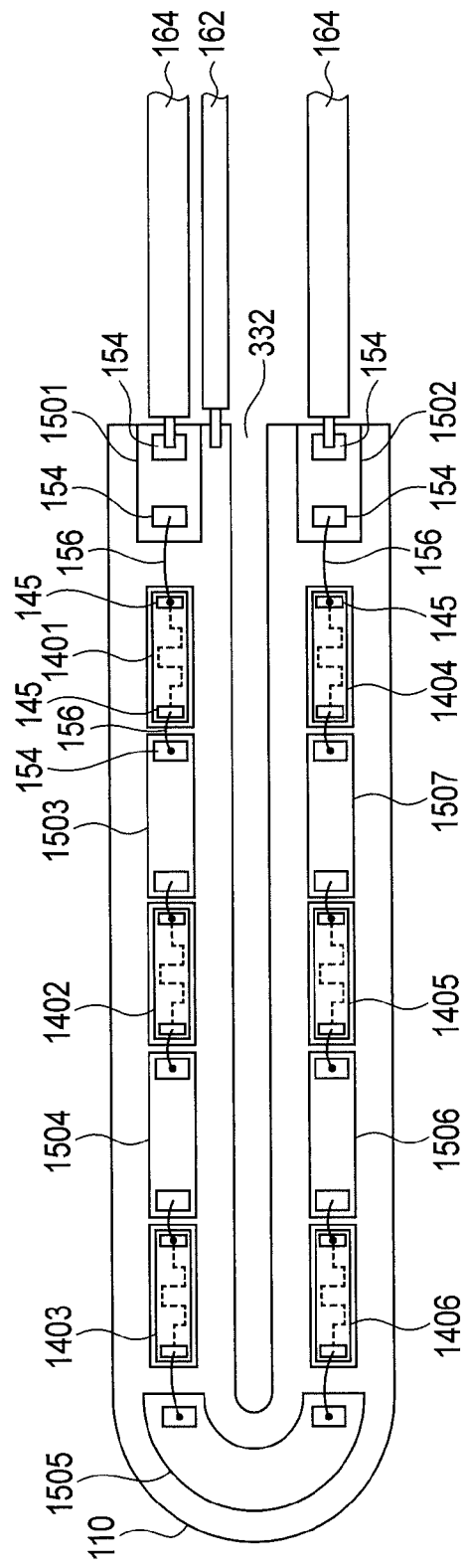
FIG. 6 is a plan view showing an outline of a structural example of a first high-frequency electrode, heat generating chips, the wiring members, various kinds of wiring lines, and other parts according to the embodiment of the present invention.

The first high-frequency electrode 110, the heat generating chips 140 on the first high-frequency electrode 110, and electrical connection concerning these members will now be described with reference to FIG. 6. As shown in FIG. 6, a planar shape of the first high-frequency electrode 110 is U-shaped so that the first cutter guide groove 332 is formed.

The six heat generating chips 140 are discretely arranged on the first high-frequency electrode 110. That is, the three heat generating chips 140 are aligned and arranged on each of two rows from the proximal end side toward the distal end side to be symmetrical with the first cutter guide groove 332 at the center. The heat generating chips 140 arranged on one row (an upper row in FIG. 6) will be referred to as a first heat generating chip 1401, a second heat generating chip 1402, and a third heat generating chip 1403 from the proximal end side. Likewise, the heat generating chips arranged on the other row (a lower row in FIG. 6) will be referred to as a fourth heat generating chip 1404, a fifth heat generating chip 1405, and a sixth heat generating chip 1406 from the proximal end side.

The wiring members 150 are arranged on the first high-frequency electrode 110 to connect the respective heat generating chips 140. The wiring members 150 are fixed by using, e.g., a resin having adhesive properties. First, the wiring member 150 is arranged at the proximal end on the side where the first heat generating chip 1401 is arranged. This wiring member 150 will be referred to as a first wiring member 1501. Likewise, a second wiring member 1502 is arranged at a proximal end on the side of the first high-frequency electrode 110 where the fourth heat generating chip 1404 is arranged.

One of the pair of first heat generating chip conducting lines 164 is electrically connected to the electrode 154 on the proximal end side of the first wiring member 1501. Likewise, the other of the pair of first heat generating chip conducting lines 164 is electrically connected to the electrode 154 on the proximal end side of the second wiring member 1502. Further, the first high-frequency electrode conducting line 162 is electrically connected to the proximal end portion of the first high-frequency electrode 110.

The electrode 154 on the distal end side of the first wiring member 1501 is electrically connected to the electrode 145 on the proximal end side of the first heat generating chip 1401 through a wire 156 formed by wire bonding. As described above, the first heat generating chip conducting line 164 is electrically connected to the first heat generating chip 1401 through the first wiring member 1501. Likewise, the first heat generating chip conducting line 164 is electrically connected to the fourth heat generating chip 1404 through the second wiring member 1502.

A third wiring member 1503 is arranged between the first heat generating chip 1401 and the second heat generating chip 1402 on the first high-frequency electrode 110. The electrode 154 on the proximal end side of the third wiring member 1503 is electrically connected to the electrode 145 on the distal end side of the first heat generating chip 1401 through the wire 156 formed by the wire bonding. Likewise, the electrode 154 on the distal end side of the third wiring member 1503 is electrically connected to the electrode 145 on the proximal end side of the second heat generating chip 1402 through the wire 156 formed by the wire bonding. As described above, the first heat generating chip 1401 and the second heat generating chip 1402 are electrically connected in series.

Likewise, a fourth wiring member 1504 is arranged between the second heat generating chip 1402 and the third heat generating chip 1403. The second heat generating chip 1402 and the third heat generating chip 1403 are electrically connected in series via the fourth wiring member 1504. A fifth wiring member 1505 is arranged between the third heat generating chip 1403 and the sixth heat generating chip 1406. The third heat generating chip 1403 and the sixth heat generating chip 1406 are electrically connected in series via the fifth wiring member 1505. Likewise, the sixth heat generating chip 1406 and the fifth heat generating chip 1405 are electrically connected in series via a sixth wiring member 1506. The fifth heat generating chip 1405 and the fourth heat generating chip 1404 are electrically connected in series via a seventh wiring member 1507. As described above, the six heat generating chips 140 are connected in series between the pair of heat generating chip conducting lines 164.

The heat generating chips 140 are connected to the control device 370 through the first heat generating chip conducting lines 164 and the cable 360. The control device 370 controls electric power that is input to the heat generating chips 140. A current output from the control device 370 flows though each resistance pattern 143 of each heat generating chip 140. As a result, each resistance pattern 143 generates heat. When the resistance pattern 143 generates heat, this heat is transferred to the first high-frequency electrode 110. This cauterizes a biological tissue that is in contact with the first high-frequency electrode 110.

The control device 370 will now be described. As shown in FIG. 7, the control device 370 comprises a control unit 371, a heat generating chip drive circuit 372, a temperature acquisition unit 373, a high-frequency energy output circuit 374, a memory unit 375, an input unit 376, a display unit 377, and a speaker 378. The control unit 371 is connected to respective units in the control device 370 and controls the respective units in the control device 370. The high-frequency energy output circuit 374 is connected to the energy treatment tool 310 and drives the first high-frequency electrode 110 and the second high-frequency electrode 210 of the energy treatment tool 310 under control of the control unit 371. That is, the high-frequency energy output circuit 374 applies a high-frequency voltage to the first high-frequency electrode 110 and the second high-frequency electrode 210 through the first high-frequency electrode conducting line 162 and the second high-frequency electrode conducting line 262.

The heat generating chip drive circuit 372 is connected to the energy treatment tool 310 and drives the heat generating chips 140 and the heat generating chips 240 of the energy treatment tool 310 under control of the control unit 371. That is, the heat generating chip drive circuit 372 supplies electric power to the resistance patterns 143 of the heat generating chips 140 and the heat generating chips 240 through the first heat generating chip conducting lines 164 and the second heat generating chip conducting lines 264 for heating under control of the control unit 371.

The temperature acquisition unit 373 has a function of acquiring a resistance value of the resistance patterns 143 of the heat generating chips 140 and the heat generating chips 240 based on a voltage applied to the heat generating chips 140 and the heat generating chips 240 and a current flowing at that moment. The resistance value of the resistance patterns 143 varies in accordance with a temperature of the resistance patterns 143. Thus, a relationship between the temperature and the resistance value of the resistance patterns 143 is acquired in advance, and this relationship is stored in the memory unit 375 in advance. The temperature acquisition unit 373 acquires the temperature of the resistance patterns 143 based on the resistance value of the resistance patterns 143 by using the relationship between the temperature and the resistance value of the resistance patterns 143. Here, a temperature of each of the first high-frequency electrode 110 and the second high-frequency electrode 210 can be considered as the temperature of the resistance pattern 143 or it can be obtained from the temperature of the resistance pattern 143. The temperature acquisition unit 373 outputs the acquired temperature of each of the first high-frequency electrode 110 and the second high-frequency electrode 210 to the control unit 371. Since each temperature is acquired based on the resistance value of the resistance patterns 143, a temperature sensor does not have to be additionally provided on the first high-frequency electrode 110, which is advantageous to miniaturization of the first electrode unit 100.

It is to be noted that the above-described temperature acquisition method is an example, and the present invention is not restricted thereto. For example, the temperature acquisition unit 373 may acquire the temperature of each of the first high-frequency electrode 110 and the second high-frequency electrode 210 based on outputs from the temperature sensors provided on the first high-frequency electrode 110 and the second high-frequency electrode 210. As each temperature sensor, for example, a thermocouple can be used. Using the temperature sensors is advantageous since it is not based on the resistance value of the resistance patterns 143, resulting that the relationship between the temperature and the resistance value of the resistance patterns 143 does not have to be provided.

The control unit 371 stores the temperatures of the first high-frequency electrode 110 and the second high-frequency electrode 210 acquired from the temperature acquisition unit 373 in the memory unit 375 and appropriately reads them out as required. The control unit 371 calculates the electric power to be input to the heat generating chips 140 and the heat generating chips 240 by using the temperatures of the first high-frequency electrode 110 and the second high-frequency electrode 210. The control unit 371 controls the heat generating chip drive circuit 372 to input the calculated electric power to the heat generating chips 140 and the heat generating chips 240.

A foot switch (SW) 380 is connected to the control unit 371, and ON that enables a treatment using the energy treatment tool 310 and OFF that stops the treatment are input from the foot switch 380. The input unit 376 inputs various kinds of settings of the control unit 371. The display unit 377 displays the various kinds of settings of the control unit 371. The memory unit 375 stores various kinds of data required for operations of the control device 370. The speaker 378 outputs an alarm sound or the like.

An operation of the therapeutic treatment apparatus 300 according to this embodiment will now be described. An operator operates the input unit of the control device 370 to set output conditions of the therapeutic treatment apparatus 300, e.g., set electric power as high-frequency energy output, a target temperature or a heating time of a thermal energy output, and others in advance. In the therapeutic treatment apparatus 300, each value may be individually set, or a set of set values according to an operative procedure may be selected. In this embodiment, the target temperature is represented as T_target.

The holding unit 320 and the shaft 340 of the energy treatment tool 310 are inserted into, e.g., an abdominal cavity through an abdominal wall. An operator manipulates the operation knob 352 to open/close the holding unit 320 and grips a biological tissue as a treatment target by using the first holding member 322 and the second holding member 324. At this time, the biological tissue as the treatment target comes into contact with the first main surface of the first high-frequency electrode 110 provided on the first holding member 322 and the first main surface of the second high-frequency electrode 210 provided on the second holding member 324.

When the biological tissue as the treatment target is gripped by the holding unit 320, the operator operates the foot switch 380. When the foot switch 380 is switched to ON, high-frequency electric power, which is a preset electric power, is supplied to the first high-frequency electrode 110 and the second high-frequency electrode 210 from the control device 370 through the first high-frequency electrode conducting line 162 running through the cable 360. The electric power to be supplied is, e.g., approximately 20 W to 80 W. As a result, the biological tissue generates heat, and the tissue is cauterized. This cauterization denaturalizes and coagulates the tissue.

Then, the control device 370 stops output of the high-frequency energy and then supplies the electric power to the heat generating chips 140 and the heat generating chips 240 so that the temperature of each of the first high-frequency electrode 110 and the second high-frequency electrode 210 can become a target temperature. Here, the target temperature is, e.g., 200° C. At this time, the current flows through the resistance pattern 143 of each heat generating chip 140 from the control device 370 via the cable 360 and the first heat generating chip conducting line 164. The resistance pattern 143 of each heat generating chip 140 generates heat by the current. The heat generated by each resistance pattern 143 is transferred to the first high-frequency electrode 110 through the substrate 141 and the bonding metal layer 149. As a result, a temperature of the first high-frequency electrode 110 rises. Likewise, the electric power is supplied to each heat generating chip 240 from the control device 370 via the cable 360 and the second heat generating chip conducting line 264, and each heat generating chip 240 generates heat. The heat generated by each heat generating chip 240 increases the temperature of the second high-frequency electrode 210.

The biological tissue that is in contact with the first high-frequency electrode 110 and the second high-frequency electrode 210 is further cauterized and coagulated by the heat described above. When the biological tissue is coagulated by heating, the output of the thermal energy is stopped. Finally, the operator operates one of the operation knobs 352 and moves the cutter 345 to cut the biological tissue. The treatment of the biological tissue is completed.

The heating treatment using the heat generating chips 140 and the heat generating chips 240 will now be described in detail. FIG. 8 is a schematic view showing a state that a biological tissue 900 is gripped by the first electrode unit 100 and the second electrode unit 200. In an example shown in FIG. 8, a heat capacity and thermal conductivity of the biological tissue 900 differ depending on each position. Here, in the biological tissue 900, a portion that is in contact with the first electrode unit 100 and has a relatively low heat capacity and relatively high thermal conductivity will be referred to as a first portion 910, and a portion that is in contact with the second electrode unit 200 and has a relatively high heat capacity and relatively low thermal conductivity will be referred to as a second portion 920. Such a case will be appropriately explained as an example.

Figure 9:
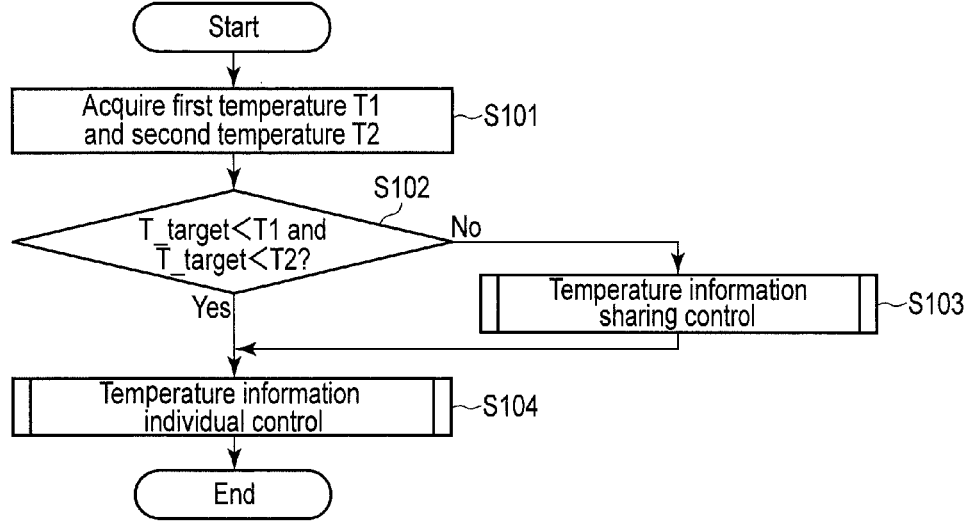
FIG. 9 is a flowchart showing an example of processing according to the embodiment of the present invention.

Temperature control of the control unit 371 over the first electrode unit 100 and the second electrode unit 200 will now be described. Here, a temperature of the first high-frequency electrode 110 that is in contact with the biological tissue 900 will be referred to as a first temperature T1, and a temperature of the second high-frequency electrode 210 that is in contact with the biological tissue 900 will be referred to as a second temperature T2. Furthermore, in this embodiment, the first temperature T1 and the second temperature T2 are assumed to be controlled to the target temperature T_target. FIG. 9 shows a flowchart of this temperature control.

At step S101, the control unit 371 acquires the first temperature T1 and the second temperature T2. The first temperature T1 and the second temperature T2 are acquired by measuring electric resistances of the heat generating chips 140 and the heat generating chips 240 that vary depending on, e.g., a temperature. It is to be noted that the method of acquiring the first temperature T1 and the second temperature T2 is not restricted thereto, and these temperatures may be acquired from, e.g., the temperature sensors provided on the first high-frequency electrode 110 and the second high-frequency electrode 210.

At step S102, the control unit 371 determines whether conditions T_target<T1 and T_target<T2 are met. If the conditions are met in the determination at step S102, the processing advances to step S104. On the other hand, if the conditions are not met in the determination at step S102, the processing advances to step S103. For example, when a heating operation is performed before this treatment, T_target<T1 and T_target<T2 can be met. However, at start of the treatment, the conditions are not generally met.

At step S103, the control unit 371 executes later-described temperature information sharing control. Then, the processing advances to step S104. At step S104, the control unit 371 executes later-described temperature information individual control. Subsequently, the processing is terminated.

Figure 10:
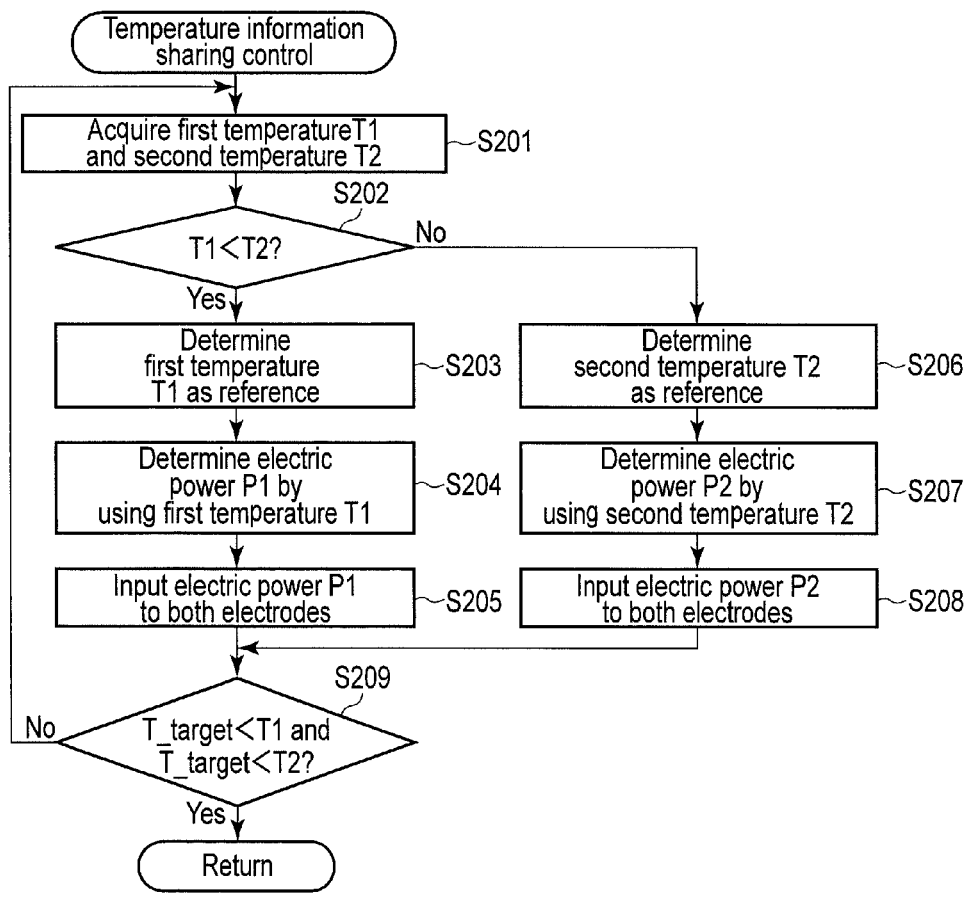
FIG. 10 is a flowchart showing an example of processing of temperature information sharing control according to the embodiment of the present invention.

The processing in the temperature information sharing control will now be described with reference to a flowchart shown in FIG. 10. At step S201, the control unit 371 acquires the first temperature T1 and the second temperature T2. At step S202, the control unit 371 determines whether a condition T1<T2 is met.

If the condition is met in the determination at step S202, the processing advances to step S203. At step S203, the control unit 371 determines the first temperature T1, which is a temperature of the first high-frequency electrode 110, as a reference temperature used for the control. At step S204, the control unit 371 determines electric power P1 that is input to the heat generating chips 140 provided on the first high-frequency electrode 110 and the heat generating chips 240 provided on the second high-frequency electrode 210 based on the first temperature T1. Here, the electric power P1 can be obtained by, e.g., the following Expression (1):

$$P1 = C1 \times dT1/dt + C2 \times (T\_target - T1) + P1now, \quad (1)$$

where C1 and C2 are predetermined control gains, and P1now is the current input power. At step S205, the control unit 371 inputs the electric power P1 to the heat generating chips 140 and the heat generating chips 240. Then, the processing advances to step S209.

If the condition is not met in the determination at step S202, the processing advances to step S206. For example, as shown in FIG. 8, if the first portion 910 that is in contact with the first high-frequency electrode 110 has a lower heat capacity and higher thermal conductivity than those of the second portion 920 that is in contact with the second high-frequency electrode 210, since the first temperature T1 of the first high-frequency electrode 110 is higher, the processing advances to step S206.

At step S206, the control unit 371 determines the second temperature T2 that is a temperature of the second high-frequency electrode 210 as a reference temperature used for control. At step S207, the control unit 371 determines electric power P2 that is input to the heat generating chips 140 provided on the first high-frequency electrode 110 and the heat generating chips 240 provided on the second high-frequency electrode 210 based on the second temperature T2. Here, the electric power P2 is obtained by, e.g., the following Expression (2):

$$P2 = C1 \times dT2/dt + C2 \times (T\_target - T2) + P2now, \quad (2)$$

where P2now is the current input electric power. At step S208, the control unit 371 inputs the electric power P2 to the heat generating chips 140 and the heat generating chips 240. Then, the processing advances to step S209. In this manner, the electric power to be input to the first electrode unit 100 and the second electrode unit 200 is determined by a feedback control based on a lower one of the first temperature T1 and the second temperature T2.

At step S209, the control unit 371 determines whether both the first temperature T1 of the first high-frequency electrode 110 and the second temperature T2 of the second high-frequency electrode 210 are higher than the target temperature T_target. That is, the control unit 371 determines whether conditions T_target<T1 and T_target<T2 are met. If the conditions are met in the determination at step S209, the temperature information sharing control is terminated, and the processing returns to step S103 described with reference to FIG. 9. On the other hand, if the conditions are not met in the determination at step S209, the processing returns to step S201.

Figure 11:
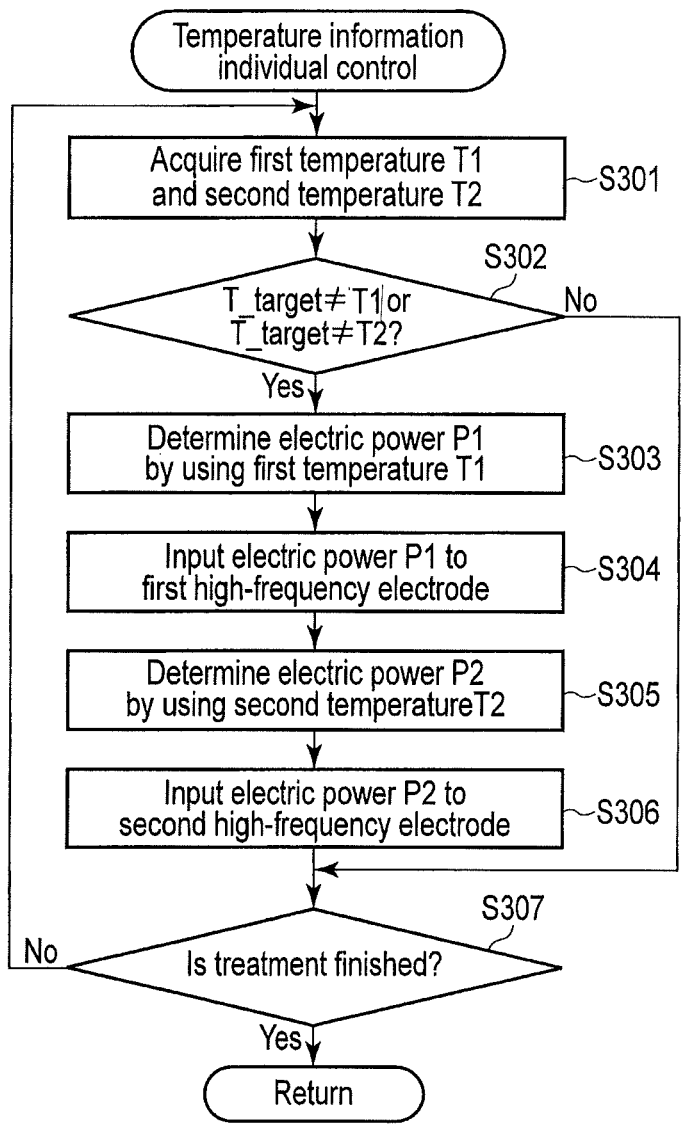
FIG. 11 is a flowchart showing an example of processing of temperature information individual control according to the embodiment of the present invention.

The processing in the temperature information individual control will now be described with reference to a flowchart shown in FIG. 11. At step S301, the control unit 371 acquires the first temperature T1 and the second temperature T2. At step S302, the control unit 371 determines whether a condition T_target≠T1 or T_target≠T2 is met. If the condition in the determination at step S302 is not met, the processing advances to step S307.

If the condition in the determination at step S302 is met, the control unit 371 determines the electric power P1 by using the first temperature T1 based on, e.g., the above Expression (1). At step S304, the control unit 371 inputs the electric power P1 to the heat generating chips 140 on the first high-frequency electrode 110. At step S305, the control unit 371 determines the electric power P2 by using the second temperature T2 based on, e.g., the above Expression (2). At step S306, the control unit 371 inputs the electric power P2 to the heat generating chips 240 on the second high-frequency electrode 210.

At step S307, the control unit 371 determines whether the treatment is terminated. This determination may be determination of whether a user has input a treatment termination command or determination of whether a treatment time has elapsed. If it is determined that the treatment is terminated, the temperature information individual control is finished, and the processing returns to step S104 described with reference to FIG. 9. On the other hand, if it is determined the treatment is not terminated, the processing returns to step S301.

FIG. 12(a) shows temperature changes of the first high-frequency electrode 110 and the second high-frequency electrode 210 in the control according to this embodiment. In FIG. 12(a), a solid line 811 indicates a change in the temperature T1 of the first high-frequency electrode 110, and a broken line 812 indicates a change in the temperature T2 of the second high-frequency electrode 210. Moreover, FIG. 12(b) shows the electric power that is supplied to each of the first high-frequency electrode 110 and the second high-frequency electrode 210 at the time of this control. In FIG. 12(b), a solid line indicates a change in amount of electric power input to the first high-frequency electrode 110, and a broken line 822 indicates a change in amount of electric power input to the second high-frequency electrode 210.

On the other hand, FIG. 13 show temperature changes of respective electrodes and changes in input power at that moment according to a comparative example. FIG. 13(a) shows temperature changes of the first high-frequency electrode 110 and the second high-frequency electrode 210. In FIG. 13(a), a solid line 831 indicates a change in the temperature T1 of the first high-frequency electrode 110, and a broken line 832 indicates a change in the temperature T2 of the second high-frequency electrode 210. Additionally, FIG. 13(b) shows the electric power supplied to each of the first high-frequency electrode 110 and the second high-frequency electrode 210. In FIG. 13(b), a solid line 841 indicates a change in amount of electric power input to the first high-frequency electrode 110, and a broken line 842 indicates a change in amount of electric power input to the second high-frequency electrode 210. In this comparative example, differing from this embodiment, the temperature information sharing control is not carried out, and the temperature information individual control alone is performed. That is, in the comparative example, the temperature control of the first high-frequency electrode 110 and the temperature control of the second high-frequency electrode 210 are individually subjected to the feedback control. Other conditions are the same as this embodiment shown in FIG. 12. In this comparative example, if the thermal conductivity of the biological tissue 900 gripped as shown in FIG. 8 is non-uniform, the electric power input to the first electrode unit 100 and the electric power input to the second electrode unit 200 differ from each other depending on a temperature difference between the first high-frequency electrode 110 and the second high-frequency electrode 210. In the example shown in FIG. 13, when the temperature of the first high-frequency electrode 110 has reached the target temperature, the electric power input to the first electrode unit 100 is reduced and, on the other hand, the electric power input to the second electrode unit that has not reached the target temperature is not reduced.

The timing at which the second high-frequency electrode 210 reaches the target temperature in this embodiment is indicated by an alternate long and short dash line in FIG. 12, and the timing at which the second high-frequency electrode 210 reaches the target temperature in the comparative example is indicated by an alternate long and two short dashes line in FIG. 12. According to this embodiment, the electric power input to the first electrode unit 100 is equal to the electric power input to the second electrode unit 200 until the temperature of the second high-frequency electrode 210 that is slow in temperature rise reaches the target temperature. As a result, a time required for both the first high-frequency electrode 110 and the second high-frequency electrode 210 to reach the target temperature from the start of heating is shorter than that in the comparative example. That is because the biological tissue is heated by heat supplied from the first electrode unit 100 that is faster in temperature rise. It is to be noted that the temperature of the first high-frequency electrode 110 temporarily rises as compared with the comparative example, but it is lowered to the target temperature after the temperature of the second high-frequency electrode reaches the target temperature, and hence this temperature rise does not adversely affect the biological tissue or the energy treatment tool 310. As described above, according to this embodiment in which the temperature information sharing control is carried out, the temperature of the biological tissue reaches a target faster than the comparative example, and the biological tissue can be efficiently heated.

It is to be noted that the same electric power is input to the first electrode unit 100 and the second electrode unit 200 in this embodiment, but the present invention is not restricted thereto. For example, the electric power input to the first electrode unit 100 and the electric power input to the second electrode unit 200 may have a predetermined ratio in accordance with characteristics of the apparatus or characteristics of the biological tissue. However, the control is easier in the situation where the same electric power is input. Further, although the control unit 371 executes the control based on an electric power value in this embodiment, it may execute control by using a voltage value.

As described above, for example, the first high-frequency electrode 110 functions as a first heat transfer unit that comes into contact with a biological tissue and transfers heat. For example, the second high-frequency electrode 210 functions as a second heat transfer unit that relatively moves with respect to the first heat transfer unit, grips a biological tissue with the first heat transfer unit, and transfers heat to the biological tissue. For example, each heat generating chip 140 functions as a first heat generating element that is arranged on the first heat transfer unit and heats the first heat transfer unit when electric power is input. For example, each heat generating chip 240 functions as a second heat generating element that is arranged on the second heat transfer unit and heats the second heat transfer unit when electric power is input. For example, the temperature acquisition unit 373 functions as a temperature acquisition unit that acquires a first temperature that is a temperature of the first heat transfer unit and a second temperature that is a temperature of the second heat transfer unit. For example, the control unit 371 functions as a control unit that compares the first temperature with the second temperature and determines a first control value concerning the electric power input to each first heat generating element and a second control value concerning the electric power input to each second heat generating element based on a lower one of the first temperature and the second temperature. For example, the heat generating chip drive circuit 372 functions as an electric power input unit that inputs the electric power having the first control value to each first heat generating element and inputs the electric power having the second control value to the second heat generating element.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A therapeutic treatment apparatus that heats a biological tissue and provides a treatment, the apparatus comprising:
    a first heat transfer surface which comes into contact with the biological tissue, the first heat transfer surface transferring heat to the biological tissue;
    a second heat transfer surface which moves relative to the first heat transfer surface, the second heat transfer surface gripping the biological tissue together with the first heat transfer unit, and the second heat transfer surface transferring heat to the biological tissue;
    a first heater configured to heat the first heat transfer surface when electric power is input to the first heater;
    a second heater configured to heat the second heat transfer surface when electric power is input to the second heater; and
    a controller configured to:
        acquire a first temperature, the first temperature being a temperature of the first heat transfer surface;
        acquire a second temperature, the second temperature being a temperature of the second heat transfer surface;
        compare the first temperature with the second temperature;
        determine a first control value concerning the electric power input to the first heater and determine a second control value concerning the electric power input to the second heater, the determination of the first and second control values being based on a lower one of the first temperature and the second temperature; and
        input the electric power to the first heater based on the first control value; and
        input the electric power to the second heater based on the second control value.

2. The apparatus according to claim 1, wherein the controller:
determines the first control value and the second control value based on the lower one of the first temperature and the second temperature; and
determines the first control value based on the first temperature and determines the second control value based on the second temperature when the first temperature and the second temperature have reached a preset target temperature.

3. The apparatus according to claim 1, wherein
each of the first heater and the second heater include an electric resistance pattern, and
each of the first control value and the second control value is one of a voltage value or an electric power value applied to the electric resistance pattern.

4. The apparatus according to claim 1, wherein
each of the first heater and the second heater includes an electric resistance pattern, and
the controller is configured to acquire the first temperature and the second temperature based on a change in resistance value of the electric resistance pattern.

5. The apparatus according to claim 1, further comprising first and second temperature sensors configured to acquire the first temperature and the second temperature, respectively.

6. The apparatus according to claim 1, wherein the controller determines the first control value and the second control value that are equal to each other based on the lower one of the first temperature and the second temperature.

* * * * *